(12) United States Patent
Wilke

(10) Patent No.: US 6,579,991 B2
(45) Date of Patent: Jun. 17, 2003

(54) METHOD AND DEVICE FOR COOLING A HOT REACTOR GAS, FOR EXAMPLE IN THE PRODUCTION OF PHTHALIC ANHYDRIDE

(75) Inventor: Alfred Wilke, Otterstadt (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/169,014

(22) PCT Filed: Dec. 29, 2000

(86) PCT No.: PCT/EP00/13329

§ 371 (c)(1), (2), (4) Date: Jun. 26, 2002

(87) PCT Pub. No.: WO01/49645

PCT Pub. Date: Jul. 12, 2001

(65) Prior Publication Data

US 2002/0193613 A1 Dec. 19, 2002

(30) Foreign Application Priority Data

Dec. 30, 1999 (DE) ......................................... 199 63 869

(51) Int. Cl.$^7$ ............................................. C07D 307/89
(52) U.S. Cl. ...................................................... 549/248
(58) Field of Search ........................................ 549/248

(56) References Cited

U.S. PATENT DOCUMENTS 3,466,300 A  9/1969  Verdrilla ..................... 260/346
5,969,160 A  10/1999  Lindström .................. 549/248

FOREIGN PATENT DOCUMENTS

EP  0 323 141  7/1989
GB  1422516  1/1976

*Primary Examiner*—Taofiq Solola
(74) *Attorney, Agent, or Firm*—Keil & Weinkauf

(57) ABSTRACT

A process for cooling a hot reaction gas, as formed, in the preparation of phthalic anhydride by oxidation of o-xylene with hot air in a reactor (213), to a predetermined inlet temperature for introduction into a separator (221), in which the separation into crude phthalic anhydride and air is then effected, is described. A simple and economical design, which can be used for comparable processes, too, of a system for cooling the hot reaction gas, which simultaneously gives rise to low maintenance costs, is obtained by locating upstream of the separator (221) a heat exchanger (227) through which a cooling medium flows, the hot reaction gas being passed through the heat exchanger (227) for interaction with the cooling medium. Especially such a system comprises in addition to a main reactor (213) a downstream reactor (241), which my have a means for intermediate cooling (243), and the gaseous cooling medium leaving the heat exchanger 227 will be fed to the main reactor (213) as reactant.

15 Claims, 10 Drawing Sheets

METHOD AND DEVICE FOR COOLING A HOT REACTOR GAS, FOR EXAMPLE IN THE PRODUCTION OF PHTHALIC ANHYDRIDE

This Appln. is a 371 of PCT/EP00/13329 filed Dec. 29, 2000.

BACKGROUND OF THE INVENTION

The present invention relates to a process and an apparatus for cooling a hot reaction gas to a predetermined inlet temperature for introduction into a separator, especially as stage in manufacturing phthalic anhydride.

The starting point of the present invention is the preparation of phthalic anhydride (PAA) by oxidation of o-xylene. Hot o-xylene and hot air are reacted in the presence of a catalyst. The PAA thus formed leaves the reactor mixed with air as hot reaction gas and has a temperature of about 360° C. In PAA plants with downstream reactors this temperature is a bit lower. The separation into crude PAA and air is then carried out in a downstream separator. Before entry into the separator(s), it is necessary to cool the hot reaction gas to a predetermined desired temperature, as a rule from about 160 to 175° C.

Usually, a complicated, at least two-stage gas cooler having at least two steam drums and corresponding cooling means is used for this purpose. This makes the process which is used for working up the reaction gas and is downstream of the actual reaction complicated and expensive.

A combination of a main reactor with a downstream reactor with or without cooling means therein has been described already; examples are the DE-A 197 42 821 and DE-A 198 07 018.

It is an object of the present invention to provide an optimized process for cooling a hot reaction gas which permits a simpler and more economical design of a reaction system with lower maintenance costs and which results in a qualitatively good and—based on the produced amounts—quantitative reaction of the educts.

We have found that this object is achieved by a process for manufacturing phthalic anhydride (PAA) by oxidation of o-xylene in the presence of a catalyst, optionally in two steps in a main and a downstream reactor, in which the hot reaction gas from the main reactor comprising o-xylene and air is cooled to a predetermined inlet temperature for introduction into a separator, wherein a heat exchanger through which a cooling medium flows is located upstream of the separator, and the hot reaction gas is passed through the heat exchanger for interaction with the cooling medium.

The heat exchanger replaces the gas cooler, with the result that the total reaction system acquires a simplified design and lower costs are to be expected.

In an embodiment of the novel process, the inlet temperature of the reaction gas on introduction into the heat exchanger is from 250 to 400° C., in PAA plants without downstream reactor preferably from 350 to 380° C. and in PAA plants with a downstream reactor preferably from 280 to 320° C., and its outlet temperature on emerging from the heat exchanger is from 130 to 180° C., preferably about 160° C. However, the heat exchanger is also capable of cooling the reaction gases or other gases at other predetermined inlet temperatures to said outlet temperature of the heat exchanger or alternatively to another outlet temperature.

It is particularly advantageous that the cooling of the reaction gas to the predetermined inlet temperature for introduction into the separator can be effected in one stage in the heat exchanger by the novel process.

According to a preferred embodiment of the novel process, a gaseous cooling medium, particularly preferably air, is used.

The inlet temperature of the cooling medium, e.g. air, on introduction into the heat exchanger may be below 100° C. and its outlet temperature on emerging from the heat exchanger may be from 300 to 350° C., preferably about 330° C. This results in a particular advantage of the novel process, whereby the cooling medium heated by the interaction with the reaction gas is in turn fed into the reactor as one of the reactants for the chemical reaction. The temperature of the cooling medium emerging from the heat exchanger is in fact, according to the novel process, about 150° C. higher than is usual in processes known from the prior art. Consequently, it has a temperature which permits direct introduction of the cooling medium into the reactor. The coolant is chosen so that it simultaneously constitutes one of the reactants of the chemical reaction.

In another embodiment part of the cooling medium is led via a by-pass around the heat exchanger and is again mixed with the heated cooling medium leaving the heat exchanger. Based on this a varying temperature of the cooling medium preferably used again in the reaction is possible. Preferably such a modification is realized by the temperature steering of the amounts passing the by-pass.

If the chemical reaction serves for preparing PAA, hot o-xylene, as one reactant, is reacted in the presence of a catalyst and hot air as a further reactant. The hot reaction gas formed as a result of the reaction essentially comprises PAA and air. Since air is simultaneously the cooling medium for the hot reaction gas and—as indicated further above—emerges from the heat exchanger at a considerably higher temperature than is possible in the prior art, it can be fed directly into the reactor. A further advantage is that the o-xylene initially having a temperature of about 30° C. is fed into the line containing the hot air and is simultaneously also heated without further apparatus and energy costs. Nevertheless, the result is an inlet temperature into the only or into the main reactor which is about 100° C. higher compared with the prior art, which leads to better utilization of the catalyst and a smaller heat-up zone in the reactor.

In contrast, it has been necessary to date in the prior art to preheat the air in an inconvenient and energy-intensive manner by means of a preheater. The liquid o-xylene preheated in a separate steam-heated heat exchanger was fed into this preheated air. However, the mixture of air and o-xylene did not reach the reactor inlet temperature achieved by the novel process. Moreover, it was found that more high-pressure steam can be generated in the reactor in the novel procedure.

Although the advantages of the novel process are presented with reference to the preparation of PAA and its advantages are described in comparison with the process known from the prior art for the preparation of PAA, the use of the apparatus necessary for cooling a hot reaction gas is not restricted to this chemical reaction. It can be used very generally for cooling hot reaction gases and can be employed for any desired chemical reaction which is carried out in a reactor at elevated temperatures and in which the cooling medium of the reaction gas emerging from the reactor, in the heat exchanger, is simultaneously required as a reactant or solvent (liquid or gaseous) for carrying out the chemical reaction.

A further achievement is an apparatus for cooling hot reaction gases to a predetermined inlet temperature for introduction into a separator after a foregoing reaction in a main reactor and optionally a following downstream reactor, comprising (a) a means for conducting the main reaction,
(b) a means for heat exchanging,
(c) optionally a downstream reactor before the means (b) and optionally having a means for intermediate cooling,
(d) a means for separating a reaction product and connections to and between the means.

The heat exchanger used can be any desired heat exchanger, for example a tubular heat exchanger. A gas/gas plate-type heat exchanger is preferably used.

The invention is to be explained in more detail below with reference to embodiments shown in the drawing.

DETAIL DESCRIPTIONS

Figure 1:
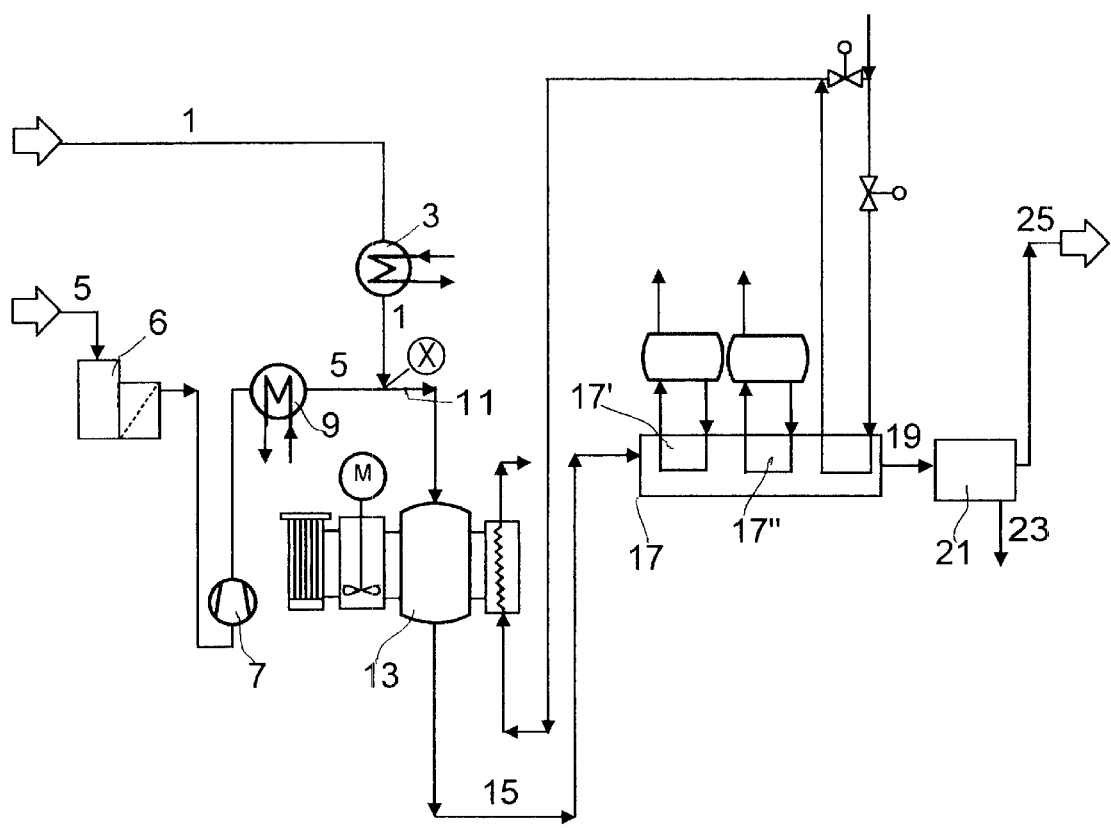
FIG. 1 shows a flow diagram of the prior art process for the preparation of PAA.

First, a reactor system as known in the prior art for the preparation is shown and explained in FIG. 1. It is known that PAA can be prepared by oxidation of o-xylene in the presence of a catalyst. Initially, the o-xylene used has a temperature of about 30° C. and is fed via line 1 to a preheater 3, which it leaves at a temperature of from about 135 to 180° C. It is then fed into line 5. Air, which initially likewise has a temperature of about 30° C., is fed in via this line 5. The air in line 5 first passes a fan 7, is heated to about 80–90° C. and then passes into a preheater 9, which it leaves again after being heated to about 150–200° C. At this time, the o-xylene having a temperature of about 135–180° C, is fed from line 3 into line 5. The air/o-xylene mixture in line 5 passes a jacket-type line heater 11 which serves for keeping the temperature of the air/o-xylene mixture at from about 160 to 175° C. and thus reaches the reactor 13 for the chemical reaction.

The reactor 13 is a tubular reactor in whose tubes the catalyst required for this oxidation reaction is present, e.g. Cs doped vanadium/titanium oxide on a carrier like steatite.

After the end of the chemical reaction, the reaction gas which has a temperature of about 350–375° C. and essentially comprises PAA and air leaves the reactor 13 via line 15; co-components are e.g. phthalide and maleic anhydride. From there, it passes to a two-stage gas cooler 17 which has two steam drums 17', 17" and is cooled to from about 160 to 175° C. Thus, the reaction gas has the predetermined advantageous temperature in order to be fed via line 19 to a separator 21. From the separator 21, crude PAA is removed via line 23 and the waste gas is fed via line 25 to an incineration or scrubbing means.

Figure 2:
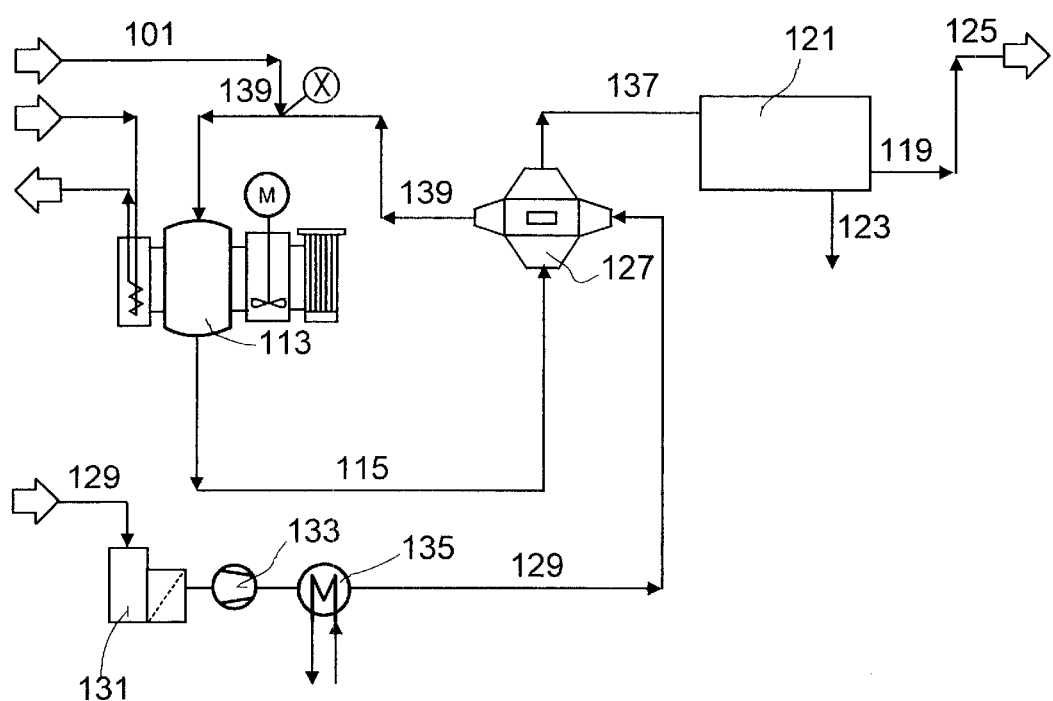
FIG. 2 shows a flow diagram according to a first embodiment of the novel process for the preparation of PAA and an apparatus therefor

In comparison, FIG. 2 shows the process and an apparatus therefor modified according to the invention. Here, those apparatus features which correspond to those shown in FIG. 1 are provided with the same reference numerals, but incremented by 100.

For the novel procedure for the chemical reaction, a one-stage heat exchanger, in this case a gas/gas plate-type heat exchanger 127, is used instead of the two-stage gas cooler. Consequently, the reaction procedure can be modified in several respects and it is therefore advantageous to describe the novel procedure for the reaction starting from the gas/gas plate-type heat exchanger 127.

The reaction gas flowing out of the reactor 113 and having a temperature of about 350–375° C. is fed via line 115 to the gas/gas plate-type heat exchanger 127. At the same time, a coolant in the form of air, having a temperature of about 90° C., flows via line 129 into the plate-type heat exchanger 127. This air coolant initially has a temperature of about 30° C. and is passed via an air filter 131 in order then to be heated to 90° C. by means of a fan 133 and a start-up heater 135. In the plate-type heat exchanger 127, heat exchange now takes place between the hot reaction gas and the air coolant. The reaction gas then leaves the plate-type heat exchanger 127 via line 137 at a temperature of about 160–175° C. The reaction gas thus has the predetermined advantageous temperature in order to be fed to the separator 121 and then be separated in the manner described above into crude PAA and waste gas. By means of the heat exchange between the hot reaction gas and the air coolant, the latter is heated to about 330° C. and can now be fed via line 139 to the reactor 113, which is designed as described above with reference to the prior art, as one of the reactants for the chemical reaction.

This means that, compared with the process known to date, the air coolant is heated about 150° higher, with the result that it can be used again as a reactant of the chemical reaction without the previously necessary energy-intensive preheating of this reactant by means of the preheater 9 which is shown in FIG. 1.

At the same time, however, the previously necessary preheating of the o-xylene by means of a further preheater, e.g. 3, is also dispensed with.

o-Xylene which is fed via line 101 passes directly into the line 139 containing the hot air coolant, and the o-xylene/air mixture required for the reaction to give PAA forms. By feeding the o-xylene having a temperature of about 30° C., the o-xylene/air coolant mixture cools to about 280° C. This temperature at which it then enters the reactor 113 is, however, still at least 100° C. higher than that possible according to the known procedure. Consequently, the catalyst in the reactor 113 can be better utilized and more high-pressure steam can be generated. Since separate o-xylene preheating by means of a preheater and e.g. the jacket heating means 11 of the line 5 leading in FIG. 1 to the reactor are dispensed with, the plant design is simpler and more economical, which is also true for the maintenance of the plant.

Figure 3:
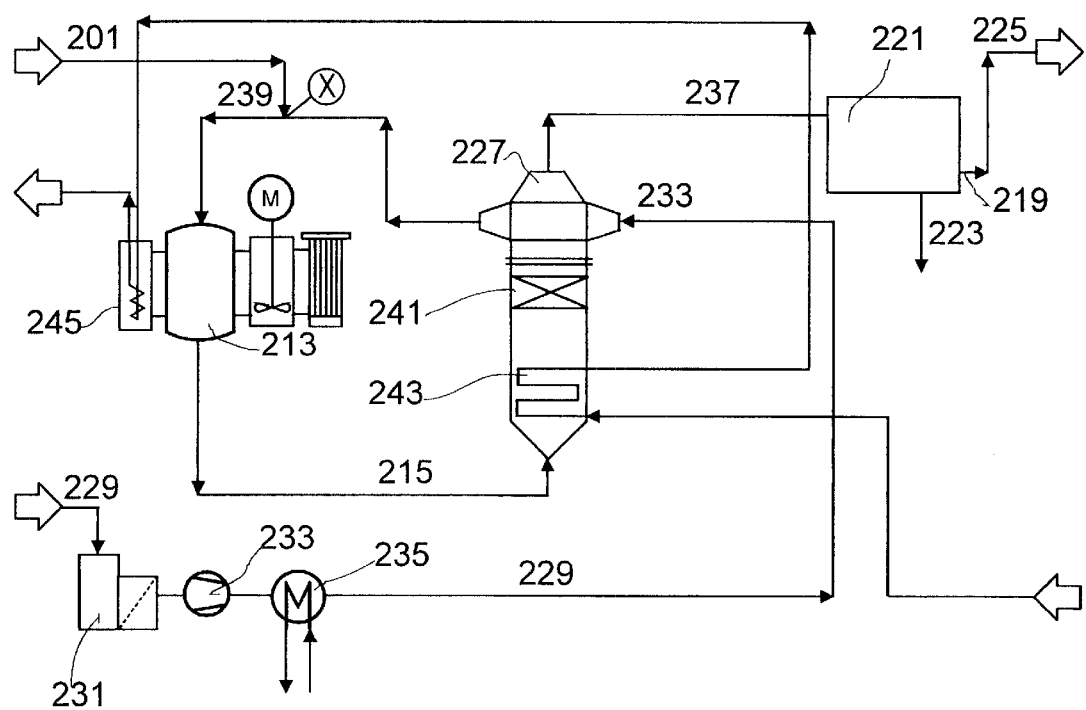
FIG. 3 shows a flow diagram according to a second embodiment of the novel process, and an apparatus therefor

FIG. 3 shows a further embodiment of the novel process and an apparatus therefor. The apparatus features identical to the embodiment according to FIG. 2 are provided with correspondingly identical reference numerals, but incremented by a hundred; the said system of reference numerals (beginning with 200) is applied in the following figures.

Figure 4:
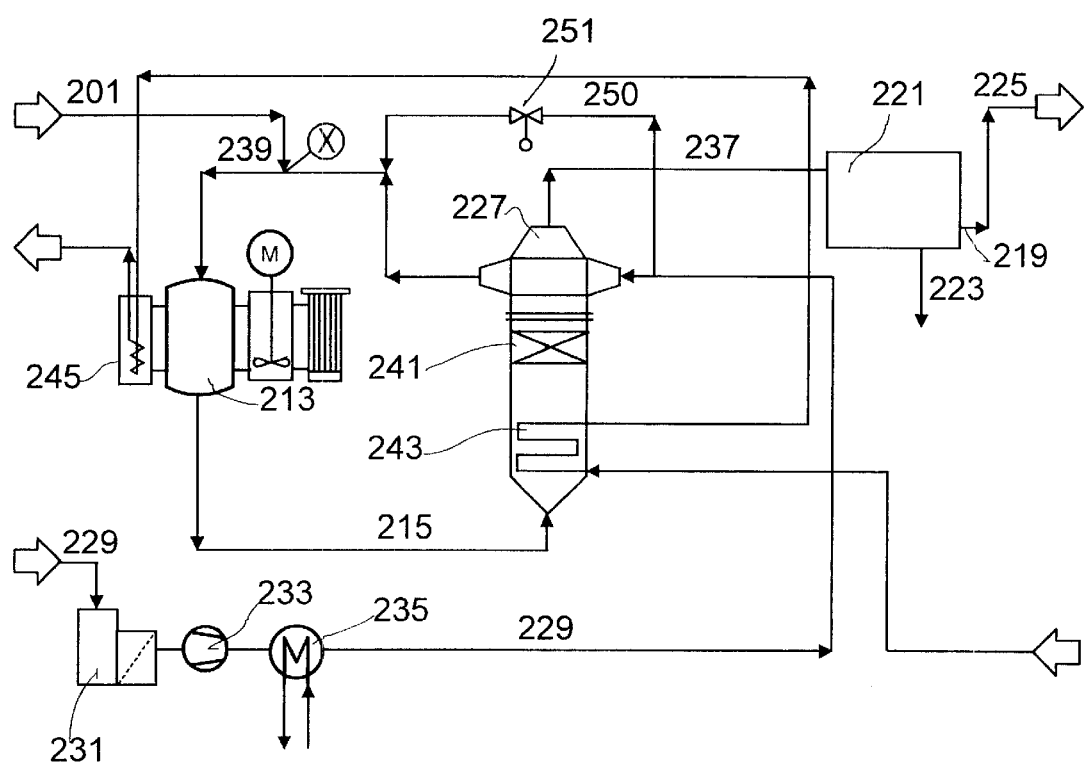
FIG. 4 shows a flow diagram according to a third embodiment of the invention including a by-pass surrounding the heat exchanger and comprising a temperature steering means FIGS. 5a, b shows a flow diagram according to a fourth embodiment of the invention (two plate-type heat exchangers including by-pass and downstream reactor)
Figure 7:
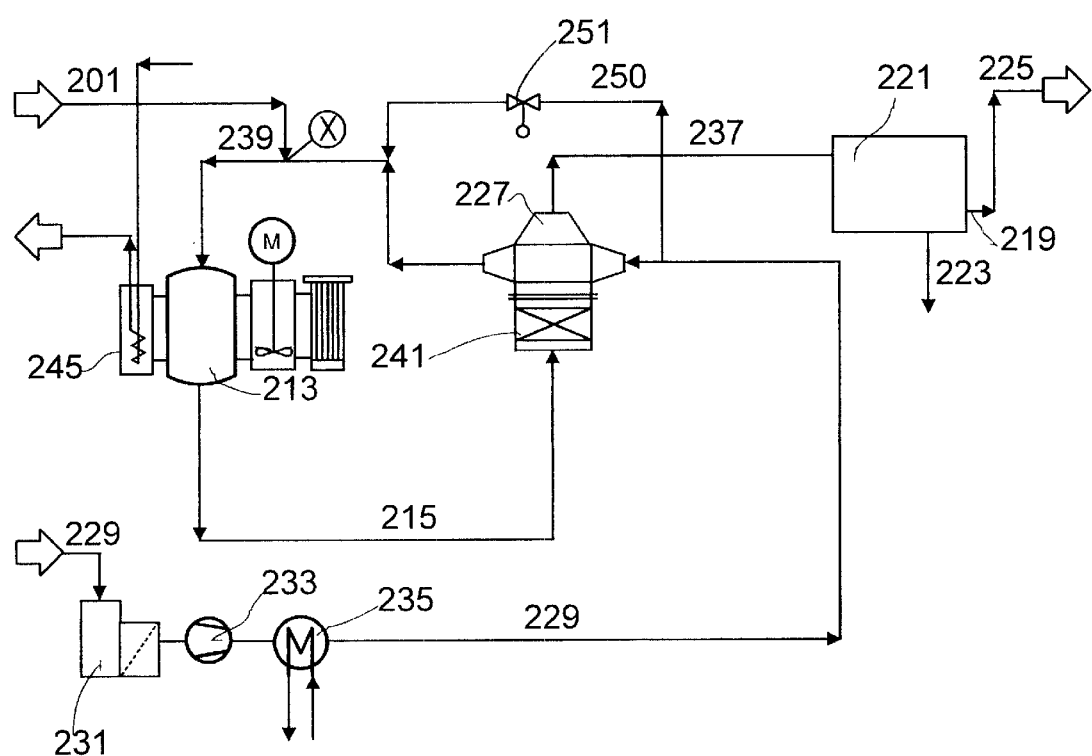
FIG. 7 shows an embodiment without a first heat exchanger

FIG. 4 shows a combination corresponding to FIG. 3 but having a by-pass 250 including a temperature steering 251, and FIG. 7 a combination different form FIG. 4 referring to the missing intermediate cooler 243.

Figure 5A:
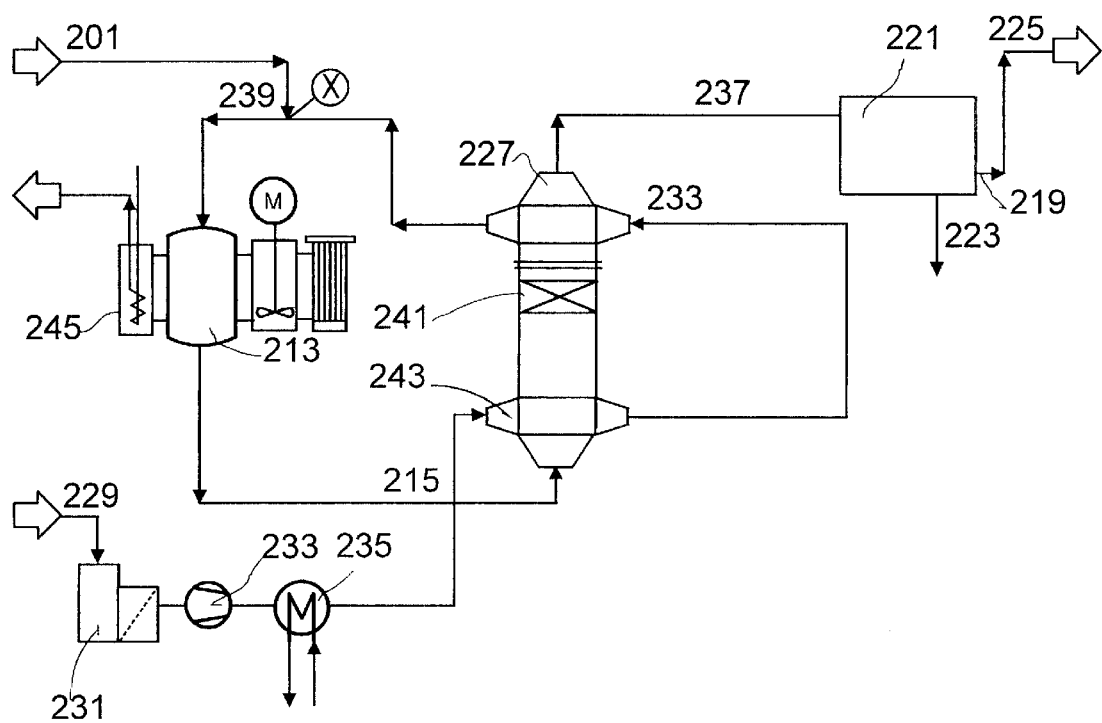
Figure 5B:
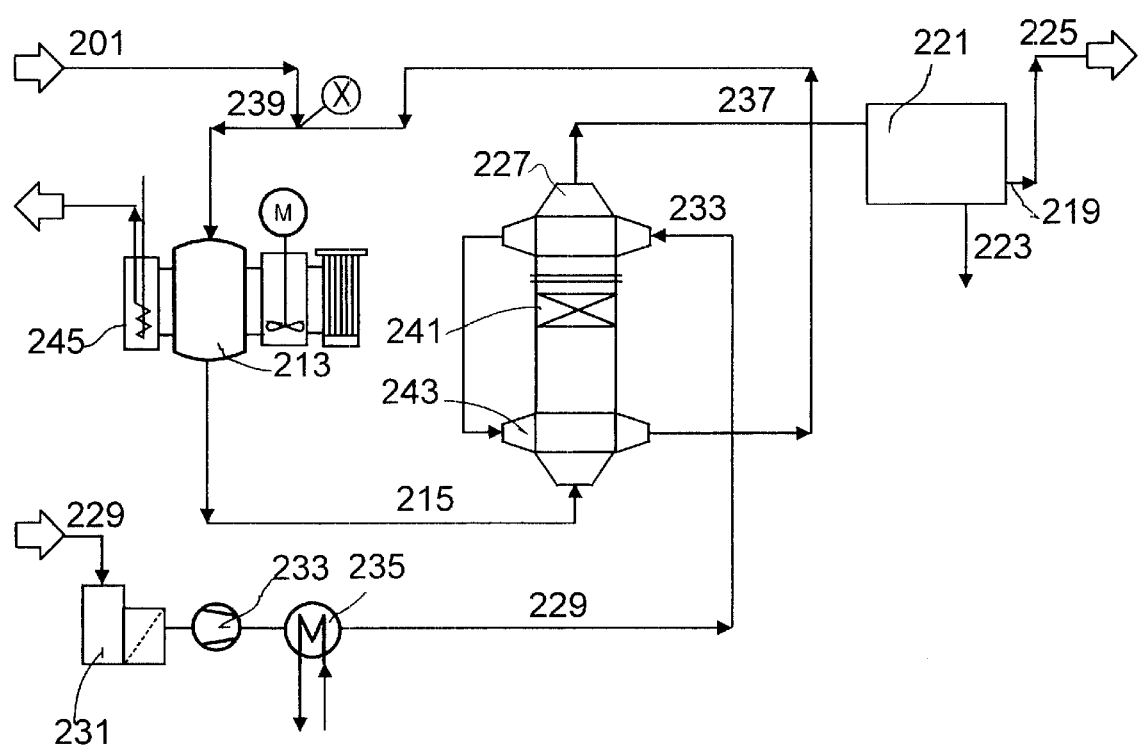
Figure 6A:
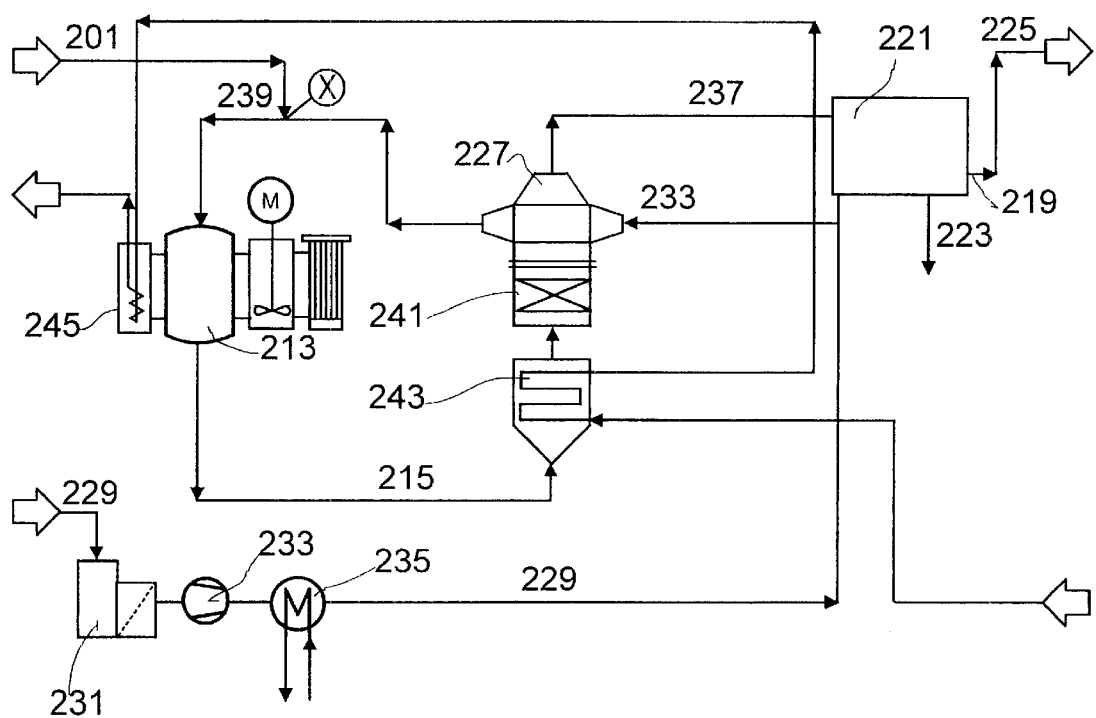
FIGS. 6a–c show embodiments of heat exchangers with downstream reactors (combinations)
Figure 6B:
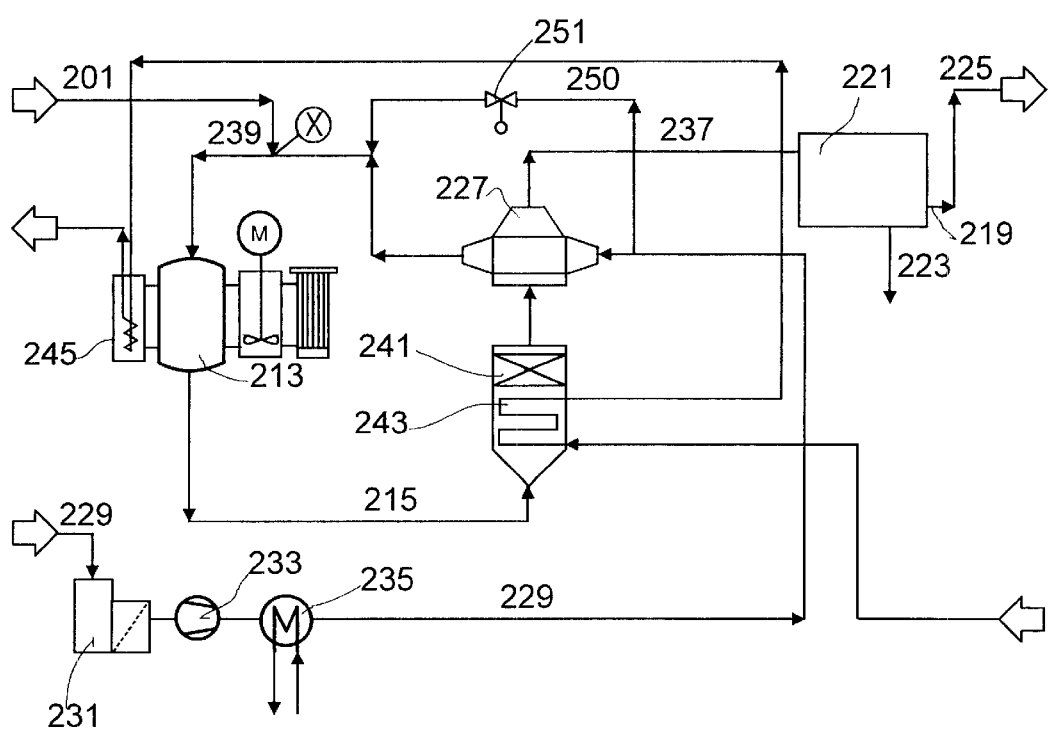
Figure 6C:
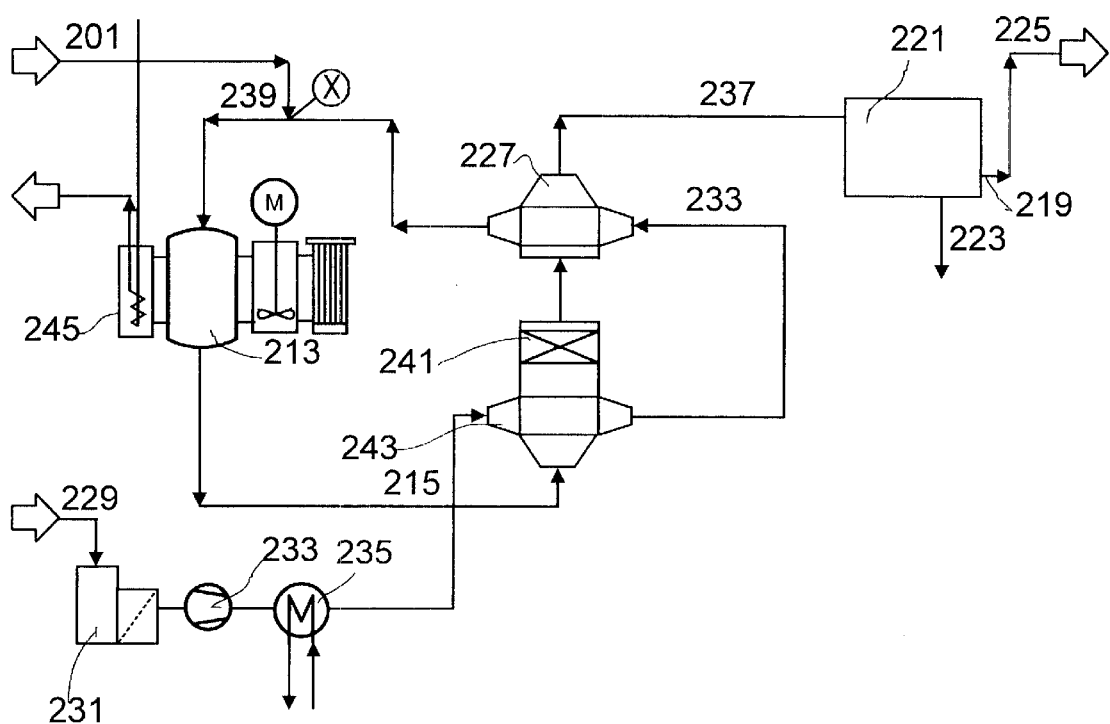

The embodiment according to FIG. 3 differs from the embodiment according to FIG. 2 in principle only in that a reactor 241 comprising the same or a different catalyst compared with main reator 213 is located downstream of the reactor 213; a usable catalyst for the downstream reactor is e.g. a non doped vanadium/titanium oxide on a carrier like silicon carbide. Since the downstream reactor 241 is to have a lower inlet temperature than the reaction gas has after its emergence from the actual reactor 213, an intermediate cooler 243 is located upstream of the downstream reactor 241. The intermediate cooler 243 may be in the form of an industrial water preheater for a salt-bath cooler 245 which is associated with the reactor 213. However, it can equally be in the form of a preheater for the air coolant, for example a further gas/gas plate-type heat exchanger or another heat exchanger type. This is shown in FIGS. 3, 5a and 5b, wherein e.g. the air coolant, leaving the plate-type heat exchanger 243 (intermediate cooler) can be fed to the second plate-type heat exchanger 227 as air coolant (FIG. 5a), or in an opposite order (FIG. 5b). There, the intermediate cooler 243, the downstream reactor 241 and the gas/gas plate-type heat exchanger 227 in the embodiment according to FIG. 3 are arranged in a common housing. However, it has been found that, for optimizing the reaction requirements, it may also be expedient to arrange the intermediate cooler 243, the downstream reactor 241 and/or the gas/gas plate-type heat exchanger 227 in separate housings. All three apparatuses can each be arranged in separate housings or in each case two of said apparatuses can be arranged together in one housing. These variants are no longer shown expressly in FIG. 6a (separation of the intermediate cooler 243 from the downstream reactor 241 and the heat exchanger 227), 6b (separation of the heat exchanger 227 from the intermediate cooler 243 and the downstream reactor 241) and 6c (as 6b, but without by-pass 250 but 243 being a gas/gas plate-type heat exchanger) all with connections between the means.

We claim:

1. A process for manufacturing phthalic anhydride (PAA) by oxidation of o-xylene in the presence of a catalyst, optionally in two steps in a main and a downstream reactor in which the hot reaction gas from the main reactor comprising o-xylene and air is cooled to a predetermined inlet temperature for introduction into a separator, wherein a heat exchanger through which a cooling medium flows is located upstream of the separator, and the hot reaction gas is passed through the heat exchanger for interaction with the cooling medium, wherein a gaseous cooling medium being air is used and wherein the cooling medium heated by the interaction with the reaction gas is fed into the reactor as one of the reactants for the chemical reaction.

2. A process as claimed in claim 1, wherein the inlet temperature of the reaction gas on introduction into the heat exchanger is from 250 to 400° C., and its outlet temperature on emerging from the heat exchanger is from 130 to 180° C.

3. A process as claimed in claim 2, wherein the inlet temperature in PAA plants without downstream reactor is from 350 to 380° C.

4. A process as claimed in claim 2, wherein the inlet temperature in PAA plants with a downstream reactor is from 280 to 320° C.

5. A process as claimed in claim 2, wherein the outlet temperature is about 160° C.

6. A process as claimed in claim 1, wherein the cooling of the reaction gas is effected in one stage.

7. A process as claimed in claim 1, wherein the inlet temperature of the cooling medium on introduction into the heat exchanger is below 100° C. and its outlet temperature on emerging from the heat exchanger is from 300 to 350° C.

8. A process as claimed in claim 7, wherein the outlet temperature is about 330° C.

9. A process for manufacturing phthalic anhydride (PAA) by oxidation of o-xylene in the presence of a catalyst, optionally in two steps in a main and a downstream reactor in which the hot reaction gas from the main reactor comprising o-xylene and air is cooled to a predetermined inlet temperature for introduction into a separator, wherein a heat exchanger through which a cooling medium flows is located upstream of the separator, and the hot reaction gas is passed through the heat exchanger for interaction with the cooling medium, wherein the inlet temperature of the reaction gas on introduction into the heat exchanger is from 250 to 400° C., and its outlet temperature on emerging from the heat exchanger is from 130 to 180° C., wherein the inlet temperature of the cooling medium on introduction into the heat exchanger is below 100° C. and its outlet temperature on emerging from the heat exchanger is from 300 to 350° C. and wherein the cooling medium heated by the interaction with the reaction gas is fed into the reactor as one of the reactants for the chemical reaction.

10. A process as claimed in claim 9, wherein the inlet temperature of the reaction gas in PAA plants without downstream reactor is from 350 to 380° C.

11. A process as claimed in claim 9, wherein the inlet temperature of the reaction gas in PAA plants with a downstream reactor is from 280 to 320° C.

12. A process as claimed in claim 9, wherein the outlet temperature of the reaction gas is about 160° C.

13. A process as claimed in claim 9, wherein the outlet temperature of the cooling medium is about 330° C.

14. A process as claimed in claim 9, wherein the cooling of the reaction gas is effected in one stage.

15. A process as claimed in claim 9, wherein a gaseous medium being air is used.

* * * * *